US010584373B2

(12) United States Patent
Shin et al.

(10) Patent No.: US 10,584,373 B2
(45) Date of Patent: Mar. 10, 2020

(54) LABEL-FREE METHODS FOR ISOLATION AND ANALYSIS OF NUCLEIC ACIDS ON SOLID PHASE DEVICE

(71) Applicant: ONE BIOMED PTE LTD., Singapore (SG)

(72) Inventors: Yong Shin, Singapore (SG); Mi Kyoung Park, Singapore (SG)

(73) Assignee: ONE BIOMED PTE LTD., Singapore (SG)

( * ) Notice: Subject to any disclaimer, the term of this patent is extended or adjusted under 35 U.S.C. 154(b) by 0 days.

(21) Appl. No.: 15/817,107

(22) Filed: Nov. 17, 2017

(65) Prior Publication Data
US 2018/0073061 A1 Mar. 15, 2018

Related U.S. Application Data

(62) Division of application No. 14/652,099, filed as application No. PCT/SG2013/000533 on Dec. 13, 2013, now Pat. No. 9,856,520.

(30) Foreign Application Priority Data

Dec. 13, 2012 (SG) .................................. 201209173

(51) Int. Cl.
| C12Q 1/6827 | (2018.01) |
| C12Q 1/686 | (2018.01) |
| C12N 15/10 | (2006.01) |
| C12Q 1/6806 | (2018.01) |
| C12Q 1/6825 | (2018.01) |

(52) U.S. Cl.
CPC ....... *C12Q 1/6827* (2013.01); *C12N 15/1006* (2013.01); *C12Q 1/6806* (2013.01); *C12Q 1/686* (2013.01); *C12Q 1/6825* (2013.01)

(58) Field of Classification Search
CPC .......................... C12Q 1/6827; C12N 15/1006
See application file for complete search history.

(56) References Cited

U.S. PATENT DOCUMENTS 8,771,938 B2 7/2014 Chang et al.

FOREIGN PATENT DOCUMENTS

| CN | 101896599 A | 11/2010 |
| WO | WO 02123185 A2 | 3/2002 |

OTHER PUBLICATIONS

Kurdistani et al, In vivo protein-protein and protein-DNA crosslinking for genomewide binding microarray, 2003, Methods,31, 90-95. (Year: 2003).*
White et al, Label-Free Detection with the Liquid Core Optical Ring Resonator Sensing Platform, Methods in Molecular Biology: Biosensors and Biodetection, 2009, 503, pp. 139-164. (Year: 2009).*
Suter et al, Label-free DNA methylation analysis using the optofluidic ring resonator sensor, 2009, SPIE 7322, Photonic Microdevices/Microstructures for Sensing, pp. 1-9 (Year: 2009).*
PCT International Search Report for PCT Counterpart Application No. PCT/SG2013/000533, 3 pp., (dated Mar. 19, 2014),
PCT Notification of Transmittal of International Preliminary Report on Patentability (Chapter II of the Patent Cooperation Treaty) for PCT Counterpart Application No. PCT/SG2013/000533, 11 pp., (dated Sep. 10, 2014).
Jonathan D. Suter, et al., "Labelfree DNA Methylation Analysis using Optofluidic Ring Resonators", Biosensors and Bioelectronics, vol. 26, pp. 1016-1020, (2010).
Yong Shin, et al., "Solid Phase Nucleic Acid Extraction Technique in a Microfluidic Chip using a Novel Non-Chaotropic Agent: Dimethyl Adipimidate", Lab on a Chip, vol. 14, pp. 359-368, (2014).
Stephen B. Baylln, "DNA Methylation and Gene Silencing in Cancer", Nature Clinical Practice Oncology, vol. 2, pp. S4-S11, (2005).
Michael T. McCabe, et al., "Cancer DNA Methylation: Molecular Mechanisms and Clinical Implications", Clinical Cancer Research, vol. 15, No. 12, pp. 3927-3937, (Jun. 15, 2009).
Matthias Wielscher, et al., "Methyl-binding Domain Protein-Based DNA Isolation from Human Blood Serum Combines DNA Analyses and Serum-Autoantibody Testing", BMC Clinical Pathology, vol. 11, No, 11, pp. 1-9, (2011).
Benjamin R. Cipriany, et al., "Real-time Analysis and Selection of Methylated DNA by 8 Fluorescence-Activated Single Molecule Sorting in a Nanofluidic Channel", PNAS, vol. 109, No. 22, pp. 8477-8482, (May 29, 2012).
James G. Herman, et al., "Methylation-specific PCR: A Novel PCR Assay for Methylation Status of CpG Islands", Proc. Natl. Acad. Sci. USA, vol. 93, pp. 9821-9826, (Sep. 1996).
Shiyang Pan, et al., "Double Recognition of Oligonucleotide and Protein in the Detection of DNA Methylation with Surface Plasmon Resonance Biosensors", Biosensors and Bioelectronics, vol. 26, pp. 850-853, (2010).
Ying-Hsu Su, et al., "Detection of Mutated K-ras DNA in Urine, Plasma, and Serum of Patients with Colorectal Carcinoma or Adenomatous Polyps", Annals of the New York Academy of Sciences, vol. 1137, pp. 197-206, (Aug. 2008).
Jonathan Daniel Suter, "Applications of the Opto-Fluidic Ring Resonator for Dna Methylation Analysis and Microfluidic Laser Development", University of Missouri, PhD Thesis, 172 pp., (Dec. 2010).
Ping-Yao Zeng, et al., "In Vivo Dual Cross-Linking for Identification of Indirect DNA-Associated Proteins by Chromatin Immunoprecipitation", BioTechniques, vol. 41, No. 6, pp. 694-698, (Dec. 2006).
Thermo Fisher Scientific Inc., "instructions: Imidoester Crosslinkers. DMA, DMP, DMS, DTBP", 2 pp., (2012).

(Continued)

*Primary Examiner* — Narayan K Bhat
(74) *Attorney, Agent, or Firm* — Womble Bond Dickinson (US) LLP

(57) ABSTRACT

Methods and system for the isolation and/or analysis of nucleic acids on a solid phase device comprising (i) incubating a nucleic acid sample with Dimethyl adipimidate (DMA) on said solid phase under conditions that allow formation of a complex of the nucleic acid with the DMA; contacting the complex of (i) with said surface; and isolating and/or analyzing the nucleic acid of the complex.

13 Claims, 4 Drawing Sheets

(56) References Cited

OTHER PUBLICATIONS

PCT Written Opinion of the International Search Authority for PCT Counterpart Application No, PCT/SG2013/000533. 5 pp., (dated Mar. 19, 2014).

First Office Action dated Nov. 15, 2016 for counterpart Chinese patent application No. 201380072172.3, 13 pgs.

Jonathan D. Suter, et al. "Label-Free Analysis of DNA Methylation using Optofluidic Ring Resonators", 31st Annual International Conference of the IEEE EMBS, Minnesota, USA, pp. 2760-2762 (Sep. 2-6, 2009).

Jonathan D. Suter, et al. "Label free quantitative DNA defection using the liquid core optical ring resonator," Science Direct Biosensors and Bioelectronics 23, pp. 1003-1009 (Oct. 22. 2007).

Daniel Robyr, et al., "Analysis of Genome-Wide Histone Acetylation State and Enzyme Binding Using DNA Microarrays," Methods in Enzymology, vol. 376, pp. 289-304 (2004).

Restriction Requirement for parent U.S. Appl. No. 14/652,099, dated Jul. 19, 2016, 9 pgs.

Office Action for parent U.S. Appl. No. 14/652,099, dated Oct. 26, 2016, 12 pgs.

Final Office Action for parent U.S. Appl. No. 14/652,099, dated Apr. 12, 2017, 24 pgs.

Advisory Action for parent U.S. Appl. No. 14/652,099, dated Jul. 10, 2017, 8 pgs.

Notice of Allowance for parent U.S. Appl. No. 14/652,099, dated Aug. 17, 2017, 13 pgs.

\* cited by examiner

A

B

LABEL-FREE METHODS FOR ISOLATION AND ANALYSIS OF NUCLEIC ACIDS ON SOLID PHASE DEVICE

CROSS-REFERENCE TO RELATED APPLICATIONS

This patent application is a divisional application of U.S. patent application Ser. No. 14/652,099, filed Jun. 12, 2015, entitled "LABEL-FREE METHODS FOR ISOLATION AND ANALYSIS OF NUCLEIC ACIDS ON SOLID PHASE DEVICE," which is a U.S. National Phase Application under 35 U.S.C. § 371 of International Application No. PCT/SG2013/000533, filed on 13 Dec. 2013, entitled LABEL-FREE METHODS FOR ISOLATION AND ANALYSIS OF NUCLEIC ACIDS ON SOLID PHASE DEVICE, which claims the benefit of priority of Singapore patent application No. 201209173-2, filed on 13 Dec. 2012.

FIELD

Methods of isolating nucleic acids preferably on a solid phase device.

BACKGROUND

Nucleic acid is an important analysis tool when identifying a disease state. DNA biomarkers (e.g. single nucleotide polymorphism (SNP), mutation, and DNA methylation) offer important clues to help researchers look for the causes of cancer and provide great opportunities to diagnose and monitor disease status during the early stages of diseases, as well as for prognosis and surveillance. Because of the extremely low physiological concentration of DNA compared to other components such as proteins (i.e. tens of nanograms of DNA versus tens of micrograms of protein in a microliter of whole blood), efficient extraction and pre-concentration of DNA from clinical samples is critical for the subsequent downstream processes such as amplification and detection. When it comes to methylated DNA this problem is magnified.

DNA methylation plays a crucial role in the regulation of gene expression and chromatin organization within normal eukaryotic cells. DNA methylation occurs by covalent addition of a methyl group at the 5 carbon of the cytosine ring, resulting in 5-methylcytosine. These methyl groups project into the major groove of DNA and effectively inhibit transcription. In mammalian DNA, 5-methylcytosine is found in approximately 4% of genomic DNA, primarily at cytosine-guanosine dinucleotides (CpGs). Such CpG sites occur at lower than expected frequencies throughout the human genome but are found more frequently at small stretches of DNA called CpG islands. These islands are typically found in or near promoter regions of genes, where transcription is initiated. In contrast to the bulk of genomic DNA, in which most CpG sites are heavily methylated, CpG islands in germ-line tissue and promoters of normal somatic cells remain unmethylated, allowing gene expression to occur. DNA methylation is mediated by a family of highly related DNA methyltransferase enzymes (DNMT), which transfer a methyl group from S-adenosyl-L_methionine to cytosines in CpG dinucleotides. The methyl-cytosines established by the DNMTs serve as binding sites for the methyl-CpG binding domain (MBD) proteins MeCP2, MBD (S. B. Baylin, DNA methylation and gene silencing in cancer. Nature Clin. Prac. Oncol. 2 (2005) 4-11; M. T. McCabe, et al., Cancer DNA methylation: Molecular mechanisms and clinical implications. Clin. Cancer Res. 15 (2009) 3927-3937; M. Wielscher, et al. Methyl-binding domain protein-based DNA isolation from human blood serum combines DNA analyses and serum-autoantibody testing. BMC Clin. Pathol. 11 (2011) 11-20; and B. R. Cipriany, et al. Real-time analysis and selection of methylated DNA by fluorescence-activated single molecule sorting in a nanofluidic channel. Proc. Nat. Acad. Sci USA. 109 (2012) 8477-8482. Through interactions with histone deacetylases, histone methyltransferases, and ATP-dependent chromatin remodeling enzymes, the MBDs translate methylated DNA into a compacted chromatin environment that is repressive for transcription. Especially, MBD is the methyl CpG binding domain of the MeCP2 protein, which binds symmetrically methylated CpGs in any sequence context, and is involved in mediating methylation dependent transcriptional repression. Although there is a strong evidence that MeCP2 binds exclusively methylated DNA fragments in vivo, a DNA methylation-independent binding activity of MeCP2 in vitro was also described in concordant literature, which makes it suitable for general in vitro DNA analysis [S. B. Baylin; McCabe, et al.; M. Wielscher, et al.; and B. R. Cipriany, et al.].

DNA methylation causes silencing of expression of tumor suppressor genes in human cancers. An ever increasing body of work within the field of epigenomics is strengthening the linkage between the hypermethylation of key nucleotide sequences and the advent of many different cancers. DNA methylation patterns in human cancer cells are considerably distorted. Typically, cancer cells exhibit hypomethylation of intergenic regions that normally comprise the majority of a cell's methyl-cytosine content. Consequently, transposable elements may become active and contribute to the genomic instability observed in cancer cells. Simultaneously, cancer cells exhibit hypermethylation within the promoter regions of many CpG island-associated tumor suppressor genes. As a result, these regulatory genes are transcriptionally silenced resulting in a loss of function. Thus, through the effects of both hypo- and hyper-methylation, DNA methylation significantly affects the genomic landscape of cancer cells, potentially to an even greater extent than coding region mutations, which are relatively rare [S. B. Baylin; McCabe, et al.; M. Wielscher, et al.; and B. R. Cipriany, et al]. DNA methylation is of great important for cancer research and clinics, since it enables earlier cancer diagnosis prior to the point of metastasis. An example is RARβ, a thyroid-steroid hormone receptor that controls the growth of many cell types by regulating gene expression. Methylation of RARβ has been reported in breast, lung, and bladder cancers.

The recent development of several genome-scale methylation screening technologies has considerably expanded our understanding of DNA methylation patterns, both in normal and cancerous cells. Particularly, MSP (methylation-specific PCR), which can rapidly assess the methylation status of virtually any group of CpG sites within a CpG island. This assay entails initial modification of DNA by sodium bisulfite, converting all unmethylated, but not methylated, cytosines to uracil, and subsequent amplification with primers specific for methylated versus unmethylated DNA. MSP requires only small quantities of DNA, is sensitive to 0.1% methylated alleles of a given CpG island locus. The chemical modification of cytosine to uracil by bisulfite treatment has provided another method for the study of DNA methylation that avoids the use of restriction enzymes. However, these methods are technically rather difficult and labor-intensive, and, without cloning of the amplified products, the technique is less sensitive than Southern analysis, requiring—25% of the alleles to be methylated for detection. Therefore, the isolation of the methylated DNA from human genomic DNA is an important step for improving of DNA methylation analysis in cancer, but that is still challenging [J. G. Herman, J. R. et al., Methylation-specific PCR: a novel PCR assay for methylation status of CpG islands. Proc. Nat. Acad. Sci USA. 93 (1996) 9821-9826; S. Pan, et al., Double recognition of oligonucleotide and protein in the detection of DNA methylation with surface Plasmon resonance biosensors. Biosens. Bioelectron. 26 (2010) 850-853; and J. D. Suter, et al., Label-free DNA methylation analysis using opto-fluidic ring resonators. Biosens. Bioelectron. 26 (2010) 1016-102].

In solution phase methods, for the isolation of the methylated DNA from genomic DNA, up to now, recombinant MBD protein, which is available upon overexpression of the cloned His-tagged protein in E. coli, has been predominantly used for DNA methylation analyses. The MBD protein has been preferably applied being immobilized in an affinity chromatography like manner with NaCl gradient elution steps to isolate methylated DNA for PCR and gel analyses in solution phase. According to commercialized protocol from companies, the MBD protein attached to Ni-Sepharose or Magnetic beads for affinity based DNA purification that enables the simultaneous analyses of the methylated DNA. MBD isolated the DNA has been found particularly suitable for DNA methylation analyses (FIG. 1, Black_line).

However, the previous studies for the detection of DNA methylation based label-free biosensor without bisulfite modification have been so far demonstrated only with synthetic oligonucleotides. The direct detection of native methylated DNAs in genomic DNA in bodily fluids such as blood, urine, or saliva would be difficult due to their extremely low concentration. The number of a specific gene in total DNA is extremely low. For instance, Su et al. have reported that about 2 copies of mutated tumor Kristin-ras DNA can be found in 50-200 µL of urine or blood samples of cancer patients [Y. H. Su, et al., Block, Detection of mutated K-ras DNA in urine, plasma, serum of patients with colorectal carcinoma or adenomatous polyps, Annals of the New York Academy of Sciences 1137 (2008) 197-206]. The sensitivity of the reported label-free biosensors is not good enough to detect such a low concentration of native DNA biomarkers. Therefore, these label-free techniques are inadequate to be used as in vitro diagnostic (IVD) device without amplification of target DNAs.

It has been recently reported that highly sensitive silicon-based microring resonators were used to detect biomolecules (e.g., protein, methylated DNA, nucleic acids) by monitoring a shift in the resonant wavelength. Optical refractive index (RI) sensors are extensively investigated for a number of applications and play a prominent role in biochemical analysis. Among the existing biochemical RI sensors, those based on integrated optical waveguides are of great interest because of their high sensitivity, small size, and high scale integration. Recently, RI sensors based on slot waveguide have attracted significant interest due to slot waveguide's remarkable property to provide high optical intensity in a sub-wavelength-size low refractive index region (slot region) sandwiched between two high refractive index strips. Using the slot as sensing region, larger light-analyte interaction, and hence higher sensitivity, can be obtained as compared to a conventional waveguide. The sensing light is concentrated close to the surface by an evanescent field undergoing exponential decay with a characteristic decay length of up to few hundred nanometers. Thus, the refractive index is affected by the binding of the analyte with immobilized capturing ligand within the decay length. Silicon microring resonators are refractive-index-based optical sensors that provide highly sensitive, label-free, real-time multiplexed detection of biomolecules near the sensor surface. Furthermore, the devices are fabricated by using standard CMOS technology, which ensures low cost and scale=up capability. The methods require time consuming steps of immobilizing probes on the surface of the device by highly skilled personnel.

The object of the invention is to ameliorate at least some of the above mentioned difficulties.

SUMMARY

Accordingly a first aspect of the invention includes a method for the isolation and/or analysis of nucleic acid molecules on a solid phase device comprising
(i) incubating a nucleic acid sample with Dimethyl adipimidate (DMA) under conditions that allow formation of a complex of the nucleic acid with the DMA;
(ii) contacting the complex of (i) with a surface of the solid phase device; and
(iii) isolating and/or analyzing the nucleic acid of the complex.

Another aspect of the invention includes a system for isolating a nucleic acid molecule of interest in a nucleic acid sample comprising:
(i) a Dimethyl adipimidate (DMA) compound capable of directly binding the nucleic acid molecule; and
(ii) a solid surface for the interaction of the nucleic acid and the DMA.

Other aspects of the invention would be apparent to a person skilled in the art with reference to the following drawings and description of various non-limiting embodiments.

BRIEF DESCRIPTION OF THE DRAWINGS

The drawings are not necessarily drawn to scale, emphasis instead generally being placed upon illustrating the principles of various embodiments. In the following description, various embodiments of the invention are described with reference to the following exemplary drawings.

DETAILED DESCRIPTION

Figure 1:
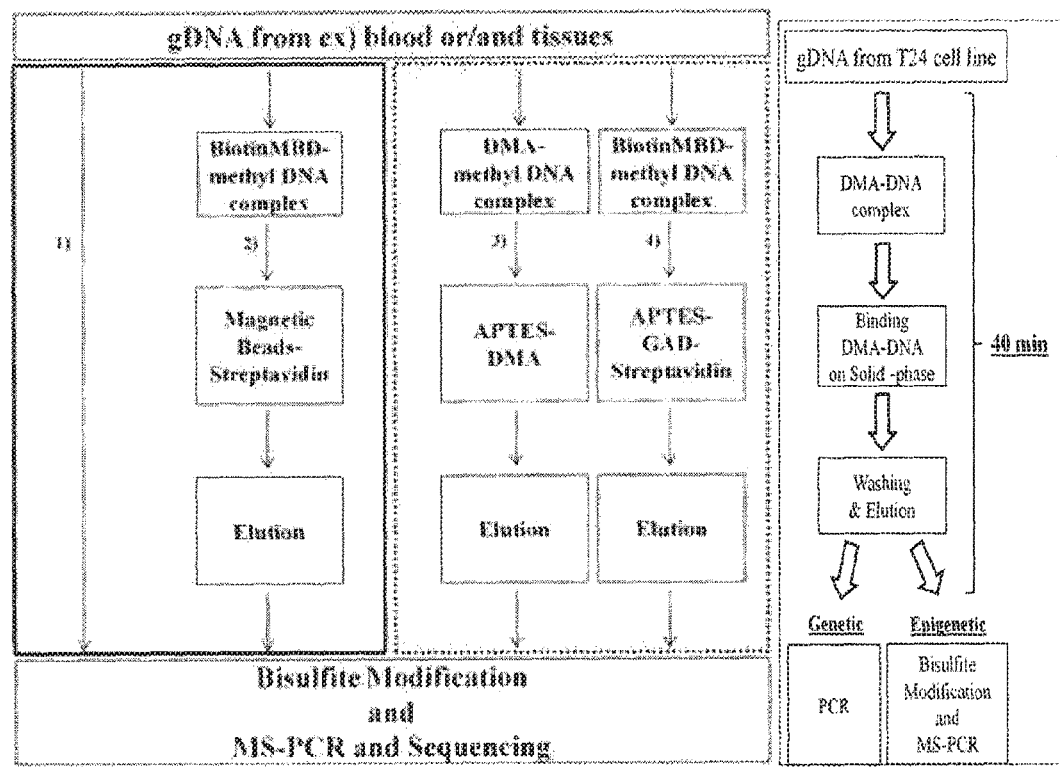
FIG. 1. Workflow for isolation and analysis of the DNA using solution phase versus solid phase methods.

Surprisingly DMA (dimethyl adipimidate) can directly bind to nucleic acid without any cross-linked protein intermediary. This direct interaction of DMA and nucleic acid can be used in a label-free method for isolation and analysis of nucleic acid or methylated DNA preferably on solid phase device including silicon, glass, polymer film, plastics, or any suitable solid phase device. The method would be very useful for DNA detection in clinical applications such as human cancer. Direct binding of nucleic acid and DMA provides a simple and cost effective chemical means of capturing and measuring nucleic acids including methylated DNA.

Accordingly a first aspect of the invention includes a method for the isolation and/or analysis of nucleic acid molecules on a solid phase device comprising
  (i) incubating a nucleic acid sample with Dimethyl adipimidate (DMA) under conditions that allow formation of a complex of the nucleic acid with the DMA;
  (ii) contacting the complex of (i) with a surface of the solid phase device; and
  (iii) isolating and/or analyzing the nucleic add of the complex.

The method allows the isolation and analysis of the nucleic acid to be performed in a real-time manner.

The term "nucleic acid" as used herein refers to an isolated nucleic acid molecule. The nucleic acid may be DNA. RNA, DNA:RNA hybrids, PNA and the like, but preferably is DNA.

The term "solid phase device" refers to a solid surface that allows the mixing of a nucleic acid sample and DMA preferably in a liquid phase. Any container that provides suitable space for an interaction between the nucleic acid sample and DMA would be suitable including silicon, glass, polymer film, plastics, or any other suitable surface. In various embodiments the solid phase device includes a microfluidic device. In various other embodiments the solid phase device includes a ring resonator, most preferably the ring resonator is silicon based. In various embodiments the ring resonator comprises a waveguide structure. In various other embodiments other suitable solid phase devices known to a person skilled in the art could be used such as for example magnetic beads.

A "nucleic acid sample" may include any biological sample including: liquid blood or, liquid saliva, urine or blood, buccal swabs, hairs, bone, teeth, fingernails, tissues from any organs (including brain), muscle, skin, tumors, unknown lumps, biopsies including needle biopsies, cells or cell lines. The sample may be taken from any biological organism, including plants, fungi and animal. The samples are preferably from vertebrates including mammals and most preferably humans. The samples are preferably from cancerous tissue or tissues suspected of being cancerous or forming neoplasm including breast cancer, lung cancer, pancreatic cancer, prostate cancer, bladder cancer, cervical cancer, nasopharyngeal cancer, hepatocellular cancer, gastric cancer, colon cancer, stomach cancer, bone cancer, testicular cancer, thyroid cancer, lymphoma, leukemia, or any other known neoplasm. In various embodiments samples may be taken from healthy non-cancerous tissue or body fluids for comparison to cancerous tissue or body fluid samples. In various embodiments nucleic acid has been extracted from the sample using methods known in the art.

Dimethyl adipimidate (DMA) comprises a membrane permeable cross linker that contains amine reactive imidoester at each end of a 6 atom spacer arm. DMA is a non-chaotropic agent for directly binding nucleic acid including methylated DNA. The DMA comprises a structure of formula I:

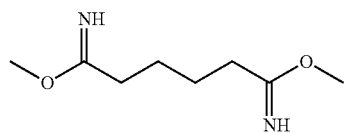

Formula I

In various embodiments the NH groups of DMA can be converted into the NH2+ groups with acids, with any suitable counter ion for example with hydrochloride salts or any other acids with a free Hydrogen group would be suitable.

Without being limited to any theories it is postulated that and the bi-functional imidoester (amine reactive group) in DMA reacts with free amino groups in DNA molecules, resulting in the cross-linking between DMA and DNA. The selective reaction between DMA and amine groups of the nucleic acid over that of protein may be related to DMA being positively charged therefore being attracted to negatively charged DNA compared to the digested negatively charged protein fragments. Additionally, the fragmented DNA during the lysis step typically contains a few base pairs of single-stranded DNA at each end of the fragment, known as "sticky" ends, and DMA reacts with amine groups of "sticky" ends. The bi-functional imidoester of DMA further provides high surface-area to volume ratio for capturing DNA.

In various embodiments the method may further comprise functionalizing the surface of the solid phase device to be aminated using surface treatments known in the art. The surface is functionalized prior to incubating the nucleic acid sample with the DMA. In various embodiments the surface is factionalized with an aminosilane preferably 3-aminopropyltriethoxysilane (APTES). The DMA will interact with the aminated surface via covalent bonds. It is observed that the bond remains or is stronger when the DMA forms a complex with nucleic acid. The complex with DMA and DNA also reacts with the amine-modified surface and forms stable covalent bonds. The bonds are amidine bonds that are reversible at high pH (>pH 10) which can be used as a means to capture and release the complex by changing the pH.

In various embodiments the nucleic acid sample is extracted with a protease prior to the incubation with the DMA, preferably proteinase K. The selective reaction between DMA and amine groups of the nucleic acid over that of protein may be related to the protease activity of proteinase K. Proteinase K both lyses cells and digests most of the protein eliminating the protein from the sample.

In various embodiments the nucleic acid comprises methylated DNA. The term "methylated DNA" has the normal meaning known in the art. Methylation of deoxyribonucleic acid (DNA) includes the addition of a methyl group on one or more cytosine or adenine at locations along a nucleotide.

In various embodiments the solid phase device is a micro fluidic device.

The term "microfluidic device" includes microchips, microchannel structures, or any suitable lab-on-a-chip platform known in the art. The DMA technique can be applied to a solid phase based microfluidic device to isolate and purify nucleic acids as well as improve DNA amplification.

In various other embodiments the solid phase device is a ring resonator.

In various embodiments all steps for isolation and analysis of nucleic acid are performed on a solid phase device. The combination of low-cost fabrication, high sensitivity and high multiplexing capability through small dimensions makes microring resonator a good candidate for disposable biosensor chips for point of care diagnostic test (POCT).

In various embodiments where the solid phase device is a ring resonator the method may further comprise
  (i) determining an output light intensity measured by a detector of an optical sensing system;

(ii) determining a change in an effective refractive index of a resonator of the optical sensing system, during the incubation;

In various embodiments the method may further comprise eluting the complex. Eluting preferably refers to removing the complex of the methylated DNA with the DMA by disrupting any covalent bond formed between the complex and a surface of the solid phase device. A means of removing the complex of the nucleic acid with the DMA from the surface includes using a high pH solution (>pH 10). One example high pH solution for removing the complex of the nucleic acid with the DMA from the surface includes disrupting any covalent bond formed between the complex and the fictionalized surface would be sodium bicarbonate.

In various preferred embodiments the method may further comprise modifying the complex at non-methylated cytosine residues. DNA methylation analysis using bisulfite conversion can modifying the complex at non-methylated cytosine residues and can operate on pictogram quantities of the input DNA, the conversion leads to modification of at least 50% of the input DNA, more preferably at least 60%, 70% or 80% of the input DNA, most preferably 90% of the input DNA.

In various embodiments the complex or the modified complex is amplified via any method known in the art. DNA amplification can be carried out by various different methods, including PCR preferably with primers specific for methylated and/or unmethylated DNA. The examples show that the efficiency of methylation specific PCR and genomic PCR amplification are enhanced by using the method.

In various embodiments the method may further comprise detecting the complex or the modified complex. Detection may be made via any method known in the art including but not limited to sequencing methods, Southern blotting analysis or any other analysis technique known in the art.

Another aspect of the invention includes a system for isolating a nucleic acid molecule of interest in a nucleic acid sample comprising:
(i) a Dimethyl adipimidate (DMA) compound capable of directly binding the nucleic acid molecule; and
(ii) a solid surface for the interaction of the nucleic acid and the DMA.

The nucleic acid sample, DMA and solid surface have the same meaning as described earlier.

In various embodiments the solid surface is functionalized. A functionalized surface is a surface that has been aminated using surface treatments known in the art.

In various embodiments the surface is factionalized with an aminosilane preferably 3-aminopropyltriethoxysilane (APTES).

In various embodiments the solid surface is on a micro fluidic device. In various other embodiments the solid surface is on a ring resonator.

In various embodiments the ring resonator is an optical detection sensor wherein said detection sensor has an altered reading when said nucleic acid molecule is bound to said DMA such that said sensor is configured to sense a complex formed between the nucleic acid molecule and the DMA.

In various embodiments the optical detection sensor is configured to resonate at a resonant wavelength.

In various embodiments the system further comprises a tunable laser capable of providing light at said resonant wavelength for the optical sensor.

In various embodiments the optical sensor or ring resonator comprises a waveguide structure.

In various embodiments said resonator has a resonant wavelength that shifts when said nucleic acid molecule is bound to said DMA, forming said complex.

In the following "Optical Sensing" will be described.

Detection of DNA methylation can be accomplished using an optically based system such as those known in the art. The system may include a light source, an optical sensor, and an optical detector. In various embodiments, the light source outputs a range of wavelengths. For example, the light source may be a relatively narrow-band light source that outputs light having a narrow bandwidth wherein the wavelength of the light source is swept over a region many times the bandwidth of the light source. In various embodiments the range of wavelengths may be (400-700 nm (visible), 700-400 (IR-A), 1260-1360 nm (O band), 1360-1460 nm (E band), 1460-1530 nm (S band), 1530-1565 nm (C band), and 1565-1625 nm (L band). This light source may, for example, be a laser. This laser may be a tunable laser such that the wavelength of the laser output is varied. In some embodiments the laser is a diode laser having an external cavity. This laser need not be limited to any particular kind and may, for example, be a fiber laser, a solid state laser, a semiconductor laser or other type of laser or laser system. The laser itself may have a wavelength that is adjustable and that can be scanned or swept. Alternatively, additional optical components can be used to provide different wavelengths. In some embodiments, the light source output light having a wavelength for which the waveguide structure is sufficiently optically transmissive. In some embodiments, the waveguide structure is within a sample medium such as an aqueous medium and the light source outputs light having a wavelength for which the medium is substantially optically transmissive such that resonance can be reached in the optical resonator. Additionally, in some embodiments, the light source output has a wavelength in a range where the complex does not have a non-linear refractive index. Likewise, in various embodiments, the light source may be a coherent light source and output light having a relatively long coherence length. However, in various embodiments, the light source may be a coherent light source that outputs light having a short coherence length. For example, in certain embodiments, a broadband light source such as a super-luminescent light emitting diode (SLED) may be used. In such cases, the wavelength need not be swept.

The light source provides light to the optical sensor. The light source may be controlled by control electronics. These electronics may, for example, control the wavelength of the light source, and in particular, cause the light source to sweep the wavelength of the optical output thereof. In some embodiments, a portion of the light emitted from the light source is sampled to determine, for example, the emission wavelength of the light source.

In some embodiments, the optical sensor comprises a transducer that alters the optical input based on the presence and/or concentration of the complex to be detected. The optical sensor may be a waveguide structure. The optical sensor may be an integrated optical device and may be included on a chip. The optical sensor may comprise semiconductor material such as silicon. The optical sensor may be an interferometric structure (e.g., an interferometer) and produce an output signal as a result of optical interference. The optical sensor may be included in an array of optical sensors.

The optical detector detects the optical output of the sensor. In various embodiments, the optical detector comprises a transducer that converts an optical input into an electrical output. This electrical output may be processed by processing electronics to analyze the output of the sensor. The optical detector may comprise a photodiode detector. Other types of detectors may be employed. Collection optics in an optical path between the sensor and the detector may facilitate collection of the optical output of the sensor and direct this output to the detector. Additional optics such as mirrors, beam-splitters, or other components may also be included in the optical path from the sensor to the detector.

In various embodiments, the optical sensor is disposed on a chip while the light source and/or the optical detector are separate from the chip. The light source and optical detector may, for example, be part of an apparatus comprising free space optics that interrogates the optical sensors on the chip, as will be discussed in more detail below.

In various embodiments, a solution such as DNA sample solution is flowed past the optical sensor. The detector detects modulation in an optical signal from the optical sensor when a complex formed between the nucleic acid and the DMA is detected.

Ring resonators offer highly sensitive optical sensors that can be prepared so as to detect a complex formed between the nucleic acid and the DMA. The operation of a ring resonator may comprise any suitable configuration. In various embodiments the optical sensor comprises an input/output waveguide having an input and an output and a ring resonator disposed in proximity to a portion of the input/output waveguide that is arranged between the input and the output. The close proximity facilitates optical coupling between the input/output waveguide and the ring resonator, which is also a waveguide. In this example, the input/output waveguide is linear and the ring resonator is circular such that light propagating in the input/output waveguide from the input to the output is coupled into the ring resonator and circulates therein. Other shapes for the input/output waveguide and ring resonator are also possible.

In various embodiments, the light injected into the waveguide input includes a range of wavelengths, for example, from a narrow band light source having a narrow band peak that is swept over time (or from a broadband light source such as a super-luminescent diode). Similarly, an output spectrum takes the form of a waveguide output. A portion of this output spectrum may be expanded into a plot of intensity versus wavelength in the spectral distribution at the resonance wavelength, of the ring resonator.

Other configurations are possible, for example, other layers may be added (or removed) or patterned differently. A portion of the substrate may have a linear waveguide and ring resonator formed thereon may be part of a larger integrated optical chip.

As is well known, light propagates within waveguides via total internal reflection. The waveguide supports modes that yield a spatially varying intensity pattern across the waveguide. A portion of the electric field and optical energy referred to as the evanescent "tail" lies outside the bounds of the waveguide. An object located close to the waveguide, for example, within this evanescent field length affects the waveguide. In particular, objects within this close proximity to the waveguide affect the index of refraction of the waveguide. The index of refraction, n, can thus be different when such an object is closely adhered to the waveguide or not. In various embodiments, for example, the presence of an object increases the refractive index of the waveguide. In this manner, the optical sensor may be perturbed by the presence of an object in the vicinity of the waveguide structure thereby enabling detection. In various embodiments, the size of the particle is about the length of the evanescent field to enhance interaction there between.

In the case of the ring resonator, an increase in the refractive index, n, increases the optical path length traveled by light circulating about the ring. Longer wavelengths can resonate in the resonator and, hence, the resonance frequency is shifted to a lower frequency. The shift in the resonant wavelengths of the resonator can therefore be monitored to determine if an object has located itself within close proximity to the optical sensor (e.g., the ring resonator and/or a region of the linear waveguide closest to the ring resonator). A binding event, whereby a complex formed between the nucleic acid and the DMA, can thus be detected by obtaining the spectral output from the waveguide output and identifying dips in intensity (or peaks in attenuation) therein and the shift of these dips in intensity.

In various embodiments, the waveguide and/or the ring resonator comprise silicon. In some embodiments, the surface of the waveguide may be natively passivated with silicon dioxide. As a result, standard siloxane chemistry may be an effective method for introducing various reactive moieties to the waveguide, which are then subsequently used to covalently fix the complex via a range of standard bioconjugate reactions.

Moreover, the linear waveguide, ring resonator, and/or additional on-chip optics may be easily fabricated on relatively cheap silicon-on-insulator (SOI) wafers using well established semiconductor fabrication methods, which are extremely scalable, cost effective, and highly reproducible. Additionally, these devices may be easily fabricated and complications due to vibration are reduced when compared to "freestanding" cavities. In one example embodiment, 8" SOI wafers may each contain about 40,000 individually addressable ring resonators. One advantage of using silicon-based technology is that various embodiments may operate in the Si transparency window of around 1.55 µm, a common optical telecommunications wavelength, meaning that lasers and detectors are readily available in the commercial marketplace as plug-and-play components.

In various embodiments the system comprises a silicon microring resonator for the label-free analysis and isolation of nucleic acid such as methylated DNA from genomic DNA from cancer samples on solid phase device. DNA methylation analysis is of great importance for cancer research and clinics, since it enables earlier cancer diagnosis prior to the point of metastasis. In order to analyze the DNA methylation, the isolation and analysis of the methylated DNA from whole genomic DNA by using high sensitivity and specificity methods are the most important factor for detection of DNA methylation. Recent reports suggest highly sensitive silicon-based microring resonators can be used to detect biomolecules (e.g., protein, methylated DNA, nucleic acids) by monitoring a shift in the resonant wavelength.

In various embodiments, light may be directed into an input of the first input/output waveguide, and, depending on the state of the first ring resonator and the wavelength of light, may be directed to either an output of the first waveguide, or may be directed into a second waveguide. For example, for the resonant wavelengths of the first ring resonator, the light may be coupled into the second waveguide instead of being output from the first waveguide at output. Light coupled into the second waveguide from the first ring resonator may be directed to either an output of the second waveguide or into the third waveguide, depending on the state of the third ring resonator. For example, for the resonant wavelengths of the third ring resonator, the light may be coupled into the third waveguide and then output at an output location. In the case where the light source that directs light into the first input/output waveguide comprises a broadband light source such as a super-luminescent diode that outputs a broadband spectrum, the light referred to above may be a wavelength component of the broader spectrum.

Other configurations can be used. A tunable laser or other tunable light source may be used as the input source and the wavelength of the output of the tunable laser can be swept. Alternatively, a broadband light source such as a super luminescent diode may be used.

More ring resonators may be added. Additionally, the ring resonators may be positioned differently with respect to each other as well as with respect to the input/output waveguide.

Various embodiments of ring resonators and possibly other geometries repeatedly circulate light around, for example, their perimeter, dramatically increasing the optical path length. Furthermore, interference between photons circulating in the structure and those traversing the adjacent waveguide create a resonant cavity of extraordinarily narrow spectral line width resulting in a high-Q device. The resulting resonance wavelengths are quite sensitive to changes in the local refractive index. As discussed herein, this sensitivity enables the sensors to detect small masses.

Therefore, the proposed concept could be very useful for DNA methylation analysis in cancer research and clinic applications.

EXAMPLES

Silicon microring resonator chips 200 mm SOI wafer with 220 nm thick top silicon layer and 2 μm think buried oxide layers by 248 nm deep UV lithography were purchased commercially then, wave-guides, and gratings were patterned thereon etched to buried oxide layer by reactive ion etching (RIE) process, followed by the deposition of 1.5 μm PECVD SiO2 as a top cladding layer. An array of microrings consisted of four rings that were connected to one common input waveguide (through) and each ring had a dedicated output waveguide (drop). Three of the four rings were used as sensor rings where windows were opened over selected individual sensor ring via the combination of dry and wet etching. One of the rings was used as a reference sensor to monitor temperature induced drift. The rings are race-track style rings with a radius of 5 μm, coupling length varied between 2 and 2.042 μm to avoid spectral overlap of resonances. The output signals of the three rings were collected via a vertical grating coupler to single-mode fiber optic probe. Insertion loss (IL) spectrum was measured with EXFO IQS-12004B DWDM passive component test system.

Figure 2:
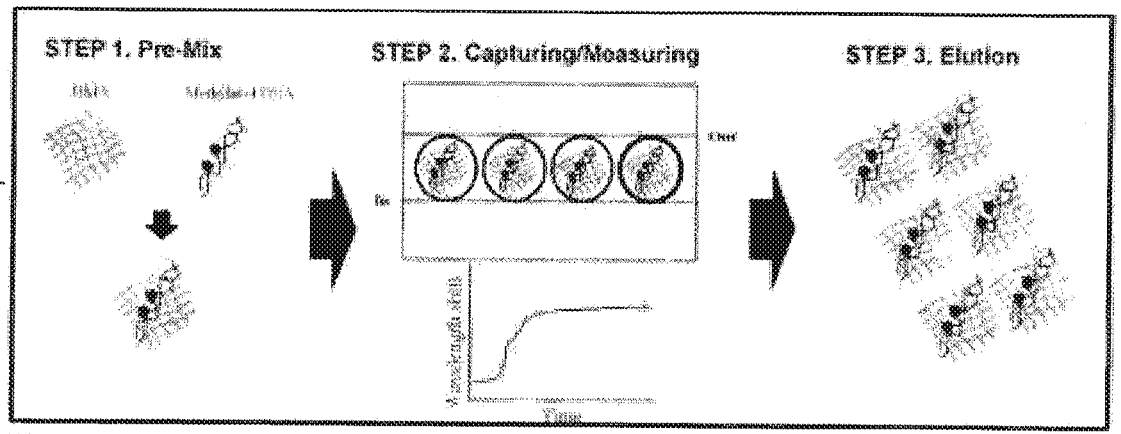
FIG. 2. Complex with DMA and the methylated DNA on solid phase device (#1). Complex with MBD protein and the methylated DNA on solid phase device (#2).
Figure 2:
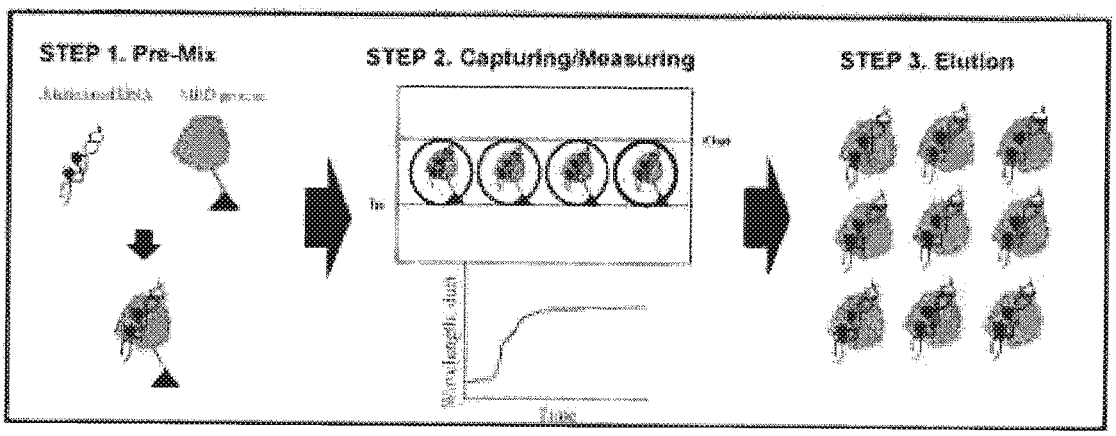

First, DMA (dimethyl adipimidate) was used as a chemical agent for capturing of the methylated DNA on silicon microring resonator, which will be monitored and analyzed the methylated DNA binding in real-time manner. The DMA has been described as a new antisickling agent by use of the bifunctional cross-linking reagents, which is known to link covalently the free amino groups in polypeptides. After capturing of the methylated DNA with the DMA, the methylated DNA is eluted by sodium bicarbonate (pH 10.6). Then, methylation specific PCR after bisulfite modification is performed to verify the efficiency for the isolation of the methylated DNA (FIG. 1, Black_round dot). The protocol was modified from those described previously. Briefly (FIG. 2, #1), the device was first treated with oxygen plasma. Then it was immersed in a solution of 2% 3-aminopropyltriethoxysilane (APTES) in a mixture of ethanol/H$_2$O(95%/15%, v/v) for 2 hours followed by thoroughly rinsing it with ethanol and de-ionized water. It was then dried under a nitrogen stream and heated at 120° C. for 15 minutes to cure the chips.

Genomic DNA was extracted from cancer cell lines (T24 and MCF7) using proteinase K and QIAamp DNA Mini Kit (Hilden, Germany). The T24 cell line, an epithelial line derived from human urinary bladder transitional cells, and the MCF7 cell line, an epithelial line derived from human mammary gland cells, were used for extraction of genomic DNA. The cancer cell lines were purchased from ATCC (American type culture collection, Manassas, Va.).

The sensor chips were then incubated with mixture of 1 ug of the genomic DNA and DMA (10 mg/ml) in PBS for 30 min. The wavelength shift was collected every 5 min up to 30 min after hybridization. After the binding, excess DNA target was rinsed free from the surface by washing the chip two times for 10 minutes each with PBS buffer and measured. Finally, the methylated DNA remained on the surface and then the methylated DNA was eluted by sodium bicarbonate (pH 10.6).

Alternatively, for the comparison the MBD protein was used for capturing of the methylated DNA on solid phase (FIG. 2, #2), not in solution phase. Briefly, the sensor surface was first functionalized with APTES, as described in above. The sensor chip was then incubated with 1 mg/mL NHS-biotin in de-ionized water for 1 h and rinsed with de-ionized water. The binding assay between biotin and streptavidin was performed by applying streptavidin solution in PBS (190 pM-950 nM). The sensor chips were then incubated with mixture of 1 μg of the genomic DNA and Biotin-MBD protein mixture in PBS for 30 min. The wavelength shift was collected every 5 min up to 30 min after hybridization. After the binding, excess DNA target was rinsed free from the surface by washing the chip two times for 10 minutes each with PBS buffer and measured. Finally, the methylated DNA remained on the surface and then the methylated DNA was eluted by sodium bicarbonate (pH 10.6). All experiments were carried out at room temperature.

Figure 3:
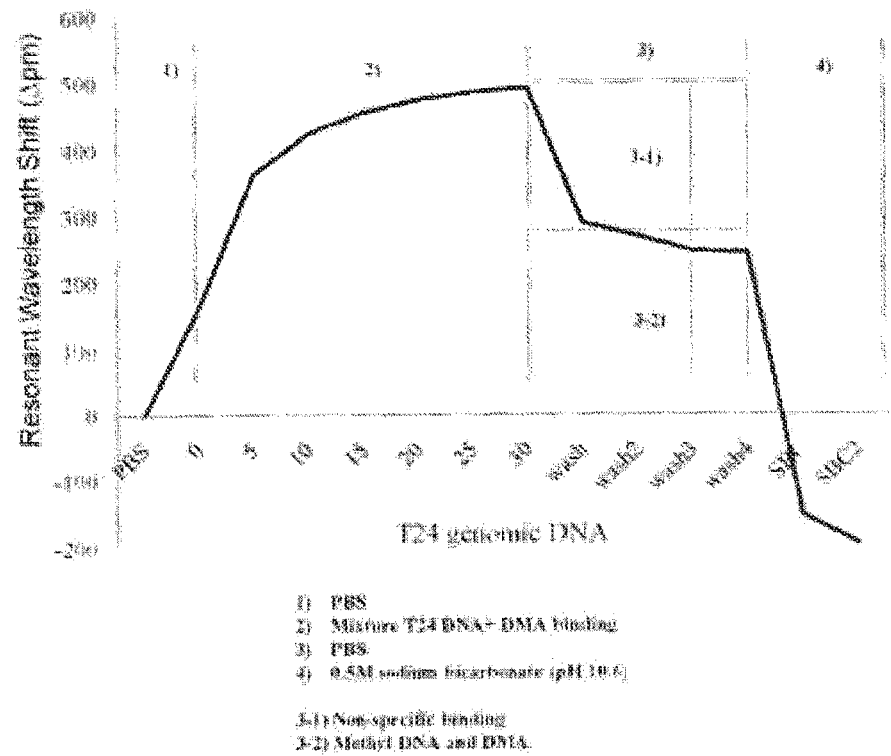
FIG. 3. Experimental result of the isolation (A) and analysis (B) of the methylated DNA on solid phase device.
Figure 3:
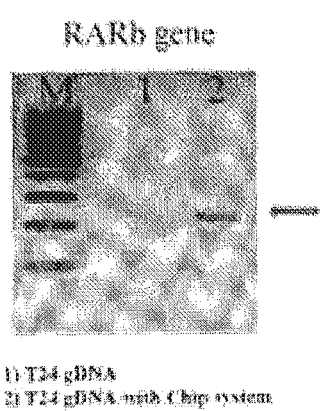
Figure 4:
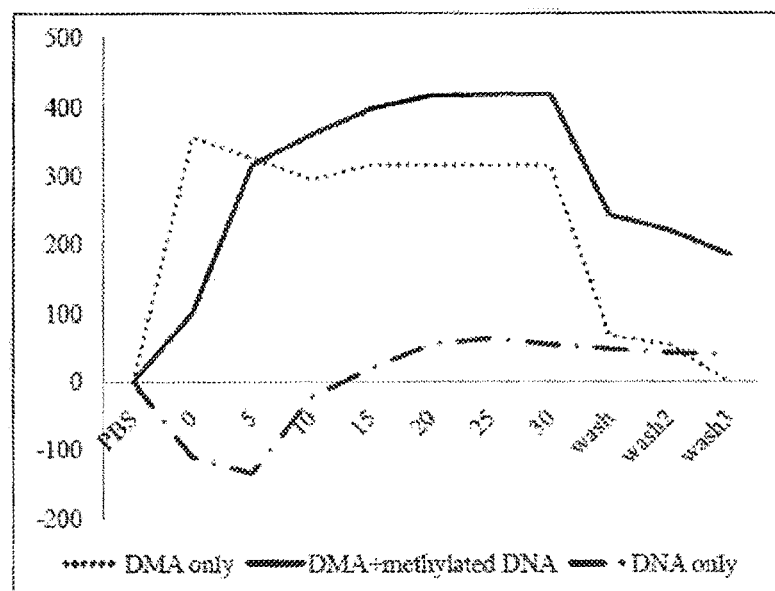
FIG. 4. Experimental result of the isolation with DMA in comparison to adding DNA alone or DMA alone (A). The wavelength shift of the methylated DNA-DMA complex in 2 cancer cell lines (B).
Figure 4:
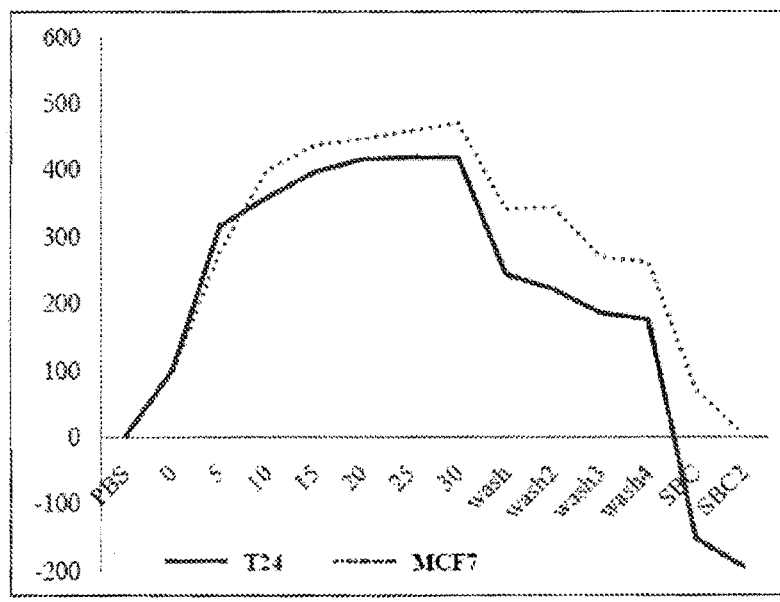

FIG. 3 shows experimental results for the method. Extracted genomic DNA from cancer cell lines such as T24 (Bladder) and MCF7 (Breast) was used for the isolation of the methylated DNA by using the solid phase device (FIG. 4B). The wavelength shift was highly observed when the sample was added and the mixture of the methylated DNA and DMA formed a complex on the functionalized solid phase surface (FIG. 3A). Then, the shift was partially reduced by washing with PBS due to getting rid of excess DNA.

The isolated DNA bound to the surface by covalent bond after washing. Finally, the DNA was collected by sodium bicarbonate for DNA analysis. The eluted DNA from T24 extracted genomic DNA was used for genetic and epigenetic analysis via conventional PCR and methylation-specific (MS)-PCR. In order to verify the efficiency of the method, Methylation specific PCR was performed for detection of the DNA methylation of the RARβ gene by using the isolated methylated DNA. The results showed that the PCR band is stronger in method (#1) than the conventional method (FIG. 3B).

In summary, new methods for isolation and analysis of the methylated DNA on solid phase device including silicon microring resonators is described. DMA is a chemical agent for capturing the methylated DNA with high specificity on solid phase device. The methods can provide not only high efficiency of the methylated DNA isolation, but also monitoring the analysis of the methylated DNA in label free and real-time manner. The method could be very useful for DNA methylation analysis in cancer research and clinic applications.

To elucidate the effect of DMA as a solid-phase-based extraction reagent, PCR-based DNA amplification was performed by using the purified or extracted DNA via the DMA method. All primers used for conventional, MS-PCR and real-time PCR of the genes (RARβ, HRAS, and Actin) are known in the art. Conventional PCR and MS-PCR were performed to verify the efficiency of the proposed technique for the genetic and epigenetic analysis. For bisulfite conversion of DNA prior to the MS-PCR operation, we used either 50 µl of purified DNA by the proposed technique or 1 µg of the extracted genomic DNA from the T24 cell line (ATCC), an epithelial cell line derived from human urinary bladder transitional cells, and the CpGenome DNA modification kit (Millipore, Billerica, Mass.). The T24 human bladder cancer cell line was maintained in plastic culture dishes with high glucose Dulbecco's modified Eagle's Medium (DMEM, Life Technology) supplemented with 10% fetal calf serum (FCS) in a 37° C. humid incubator with 5% ambient $CO_2$. The cancer cell lines were cultured, and then the genomic DNA was extracted by using AL buffer with proteinase K from a QIAmp DNA mini kit (Qiagen, Hilden, Germany). Briefly, for genetic analysis of HRAS gene, 2 µl of the eluted DNA from each sample such as the complex, DMA alone, and DNA alone was amplified in a total volume of 25 µl containing 1×PCR buffer (Qiagen, Hilden, Germany), 2.5 mM $MgCl_2$, 0.25 mM deoxynucleotide triphosphate, 25 pmol of each primer (for HRAS gene), and 1 unit of Taq DNA polymerase (Qiagen, Hilden, Germany) at 95° C. for 15 min; 35 cycles of 95° C. for 30 s, 60° C. for 30 s, and 72° C. for 30 s; and a final elongation step at 72° C. for 7 min. For the epigenetic analysis of RARβ gene, 2 µl of bisulfitemodified DNA from either conventional (no purification step) or the proposed DMA method was amplified in a total volume of 25 µl containing 1×PCR buffer (Qiagen, Hilden, Germany), 2.5 mM MgCl2, 0.25 mM deoxynucleotide triphosphate, 25 pmol of each primer (for RARβ gene), and 1 unit of Taq DNA polymerase (Qiagen, Hilden, Germany) at 95° C. for 15 min; 45 cycles of 95° C. for 30 s, 59° C. for 30 s, and 72° C. for 30 s; and a final elongation step at 72° C. for 7 min. PCR amplicons were visualized by gel electrophoresis, which was used to separate PCR products on a 2% agarose gel containing ethidium bromide (EtBr) (Sigma-Aldrich). The gel was visualized using a Gel Doc System (Bio-Rad). The band intensity was calculated by Image J (National Institute of Health, USA). Determination of DNA concentration and purity was done by UV spectrophotometer. Real-time PCR was performed to verify the efficiency of the 3 different extraction methods.

The target template for RT-PCR was obtained from human genomic DNA extracted from either whole blood or urine samples. For real-time PCR, the following procedure is modified from the protocol supplied with LightCycler 2.0 (Roche Diagnostics). Briefly, 5 µl of DNA was amplified in a total volume of 20 µl, containing 4 µl of LightCycler FastStart DNA Master mix, 25 pmol of each primer, and 2 µl of DNA template. An initial pre-incubation cycle of 95° C. for 10 min was followed by 45 cycles at 95° C. for 10 s, and 60° C. for 30 s (for HRAS and Actin genes); and by a cooling step at 40° C. for 30 s. The amplified products with SYBR Green signals were carried out on a LightCycler 2.0.

The DMA technique in microfluidic chips was compared with 2 different DNA extraction methods (QIAmp DNA mini kit in solution phase and a chaotropic reagent (ethanol) on a micro-chip) to validate the efficiency of the DMA reagent in SPE of DNA from human whole blood and urine samples in micro-chips (FIG. 4A). First, either 2 µl of whole blood (with 8 µl of PBS) or 10 µl of urine (without pH adjustment) were used for DNA extraction in microfluidic chips. For obtaining the extracted DNA, the process consisting of five steps was followed: (1) filtering and separating the cells based on their size, (2) lysing the cells, (3) binding the DNA with either a chaotropic reagent or DMA, (4) washing and purifying the DNA, and (5) eluting the DNA with either distilled water or elution buffer. After elution of the extracted DNA, the purity of the DNA extracted by the 3 different techniques was measured determining the ratio of the optical densities of the samples at 260 nm (DNA) and 280 nm (protein). The quality of the DNA from the DMA technique in both blood and urine was statistically significant induced purity for the sample ($p<0.001$) compared to that obtained from the ethanol based chaotropic method. In fact, since the urine medium is relatively clean and contains few proteins compared to blood, it was expected that the effectiveness of the DMA-based SPE on the quality of DNA extracted from the blood sample over other methods would be more pronounced than that from the urine sample. In contrast to expectation, highly purified DNA by the proposed technique was obtained from both the whole blood and urine samples. It is assumed that this is because the DMA tightly binds with DNA molecules extracted from the fluids samples during the washing step to get rid of other molecules such as cell debris, proteins, and so on, compared to the chaotropic method. Next, the amplification test was performed with the extracted DNA using RT-PCR. Both HRAS and Actin genes were used as genetic targets and amplified in all DNA samples extracted by using the 3 different techniques. It was shown that the quantity and quality of the DNA extracted with the DMA-based technique was greater than that obtained by the other methods. For real-time (RT)-PCR, 2 µl of DNA extract from total DNA sample groups was used without any quantification in order to mimic the real situation for the micro total analysis system in which the extracted DNA from the device is more likely directly used as a target template without any quantification for genetic analysis in clinical settings. Thus, the SYBR fluorescence signal in use of the QIAmp DNA mini kit (DNA extracted from 200 µl of whole blood or urine) appeared to be saturated at an earlier Ct (cycle threshold) value than others. It was observed that the DNA biomarkers (HRAS, Actin) for the genetic analysis were amplified with good quality and quantity by using the DMA-based technique. Therefore, the proposed DMA technique in this study can be useful for the solid phase DNA extraction with high quality from a small volume of human body fluids in a micro-chip system.

Design and Fabrication of Silicon Microfluidic Devices

For testing DMA-based method in a microchip environment, silicon based DNA extraction microfluidic devices was used. The structure and fabrication of the DNA extraction microfluidic devices are known. The silicon microfluidic chip comprises three components, including (1) prefiltration part for cell separation; (2) micromixer consisting of a two-stage spiral mixer for cell lysis; and (3) a meander-shaped microchannel for DMA-based method for maximization of the $SiO_2$ surface area, which is estimated to be over 60 mm2. The microfluidic chips were fabricated using a reactive ion etching (RIE) process on the front side of the silicon substrate overlaid with 2 µm-thick thermal $SiO_2$ as a hard masking layer. To form the fluidic interconnections, a wet etch process with potassium hydroxide (KOH) was applied to the back side of the silicon substrate overlaid with a composite masking layer of silicon nitride (Si3N4) deposited by low pressure chemical vapor deposition (LPCVD) over a thermal SiO$_2$ layer. With the remaining SiO$_2$ thin film layer on the micro channel surface, an anodic bonding process with a Pyrex glass substrate was performed to cap the open channel. The overall size of each fabricated microfluidic device is 16 mm×12 mm×1.2 mm.

The microfluidic device process flow for DNA extraction from human body fluids (whole blood or urine) with a small sample volume includes the following steps that were modified from previously reported protocol.24-35 The microfluidic chips are packaged in a polycarbonate housing, which includes o-rings with drilled holes for fluidic interconnection from external syringe pumps to the bottom of the silicon micro-chip. All samples and reagents are sequentially delivered to the microchip in the following order Inlet I: separation—injecting the samples into the microfilter to separate cells by size; Inlet II: secretion—injecting the AL buffer with proteinase K to be used as a lysis buffer into the micromixer Inlet III: washing and elution—injecting the wash buffers (either EtOH or DMA and PBS) to purify the sample; and Outlet IV: eluting the nucleic acid from silicon solid surface. When using a chaotropic method (ethanol), either the whole blood (2 µl) with 8 µl of PBS buffer or urine (10 µl) were injected with a syringe pump (KD Scientific. MA) into Inlet I at a flow rate of 1.67 µl min-1 for 10 min. Then, lysis buffers were injected into Inlet II at a flow rate of 3 µl min-1 for 10 min, with an increase in Inlet I flow rate to 3 µl min-1 for 10 min with PBS buffer by syringe pumps. Ethanol was added to Inlet III at a flow rate of 10 µl min-1 for 10 min during the lysis reaction. Then, ethanol alone was sequentially used for washing through the chip at 12.5 µl min-1 for 5 min. Finally, the extracted DNA was eluted with pure water at 12.5 µl min-1 for 10 min.

When using the proposed DMA method, the microchannel (Inlet III) part was first coated with APTES for 2 h with a syringe pump, and the surface was washed with ethanol for 20 min. Then the surface was dried with nitrogen gas to ready for reaction. Either the whole blood (2 µl) with 8 µl of PBS buffer or urine (10 µl) was injected with a syringe pump into Inlet I at a flow rate of 1.67 µl min-1 for 10 min. Lysis buffers were then injected into Inlet II at a flow rate of 3 µl min-1 for 10 min, and the Inlet I flow rate was increased to 3 µl min-1 for 10 min with PBS buffer by syringe pumps. DMA solution (25 mg mL-1) was added to Inlet III at a flow rate of 10 µl min-1 for 10 min during the lysis reaction. Then, the PBS buffer was sequentially passed through the chip, at 12.5 µl min-1 for 10 min, in order to get rid of non-specific bound molecules and PCR inhibitors. Finally, the extracted DNA was eluted with elution buffer at 12.5 µl min-1 for 10 min. In addition, 200 µl of whole blood or urine was used for genomic DNA extraction as reference material using a QIAmp DNA mini kit (Hilden, Germany). All extracted DNA was then used for genetic analysis by RT-PCR.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

What is claimed is:

1. A method of isolating a nucleic acid molecule on a solid phase device, the method comprising:
    incubating a nucleic acid sample with dimethyl adipimidate (DMA) under conditions which allow the DMA to bind directly to the nucleic acid molecule to form a complex of the nucleic acid molecule with the DMA;
    contacting the complex with a surface of the solid phase device; and
    isolating the complex from the surface using an elution solution having a pH of more than 10.

2. The method according to claim 1, wherein a surface of the solid phase device is functionalizing prior to the incubation.

3. The method according to claim 1, wherein the nucleic acid sample is extracted with a protease.

4. The method according to claim 3, wherein the protease is proteinase K.

5. The method according to claim 1, wherein the nucleic acid molecule comprises methylated DNA.

6. The method according to claim 1, wherein the solid phase device is a microfluidic device.

7. The method according to claim 1, wherein the solid phase device is a ring resonator.

8. The method according to claim 7, further comprising determining an output light intensity measured by a detector of an optical sensing system;
    determining a change in an effective refractive index of a resonator of the optical sensing system, during the incubation.

9. The method according to claim 7, wherein said ring resonator comprises a waveguide structure.

10. The method according to claim 1 wherein the complex is modified at non-methylated cytosine residues.

11. The method according to claim 1 wherein the complex or the modified complex is amplified.

12. The method according to claim 1 wherein the complex or the modified complex is detected.

13. The method according to claim 1, further comprising: analyzing the nucleic acid molecule of the complex.

* * * * *